(12) United States Patent
Singh et al.

(10) Patent No.: US 9,056,775 B2
(45) Date of Patent: Jun. 16, 2015

(54) PROCESS FOR THE PREPARATION OF INORGANIC HYDROGELS WITH ALKALI HALIDES

(75) Inventors: Ajeet Singh, Gujarat (IN); Bishwajit Ganguly, Gujarat (IN)

(73) Assignee: Council of Scientific and Industrial Research, New Delhi (IN)

( * ) Notice: Subject to any disclaimer, the term of this patent is extended or adjusted under 35 U.S.C. 154(b) by 373 days.

(21) Appl. No.: 13/583,030

(22) PCT Filed: Mar. 10, 2011

(86) PCT No.: PCT/IB2011/000506
§ 371 (c)(1),
(2), (4) Date: Nov. 19, 2012

(87) PCT Pub. No.: WO2011/110931
PCT Pub. Date: Sep. 15, 2011

(65) Prior Publication Data
US 2013/0121906 A1    May 16, 2013

(30) Foreign Application Priority Data
Mar. 12, 2010  (IN) .............................. 579/DEL/2010

(51) Int. Cl.
  *C01B 25/30*   (2006.01)
  *A61L 27/52*   (2006.01)

(52) U.S. Cl.
  CPC ............... *C01B 25/308* (2013.01); *A61L 27/52* (2013.01); *C01B 25/306* (2013.01)

(58) Field of Classification Search
  CPC ................ C01B 25/30–25/308; C01B 25/395; C01B 25/425; C01B 25/445; C01D 13/00
  See application file for complete search history.

(56) References Cited

U.S. PATENT DOCUMENTS

| 1,688,112 A |   | 10/1928 | Booth et al. |
| 3,421,845 A |   | 1/1969 | Peterson |
| 5,955,047 A | * | 9/1999 | Yamada et al. ............... 423/305 |

FOREIGN PATENT DOCUMENTS

| CA | 890 813 A | 1/1972 |
| EP | 0 240 635 A1 | 10/1987 |

* cited by examiner

Primary Examiner — Anthony J Zimmer
Assistant Examiner — Justin Bova
(74) Attorney, Agent, or Firm — Ladas & Parry LLP

(57) ABSTRACT

The present invention relates to a process for preparing inorganic hydrogels with alkali halides such as common salt (NaCl) and methods of making such hydrogels. The present invention provides hydrogels that may be formed by the self-assembly or may be brought about by a change in one or more characteristics of the solution. A characteristic of the solution that may change includes pH, temperature, and concentration of one or more specific ion. This invention further discloses the use of only inorganic components towards the formation of inorganic hydrogels.

11 Claims, 4 Drawing Sheets

US 9,056,775 B2

PROCESS FOR THE PREPARATION OF INORGANIC HYDROGELS WITH ALKALI HALIDES

RELATED APPLICATION INFORMATION

Figure 1:
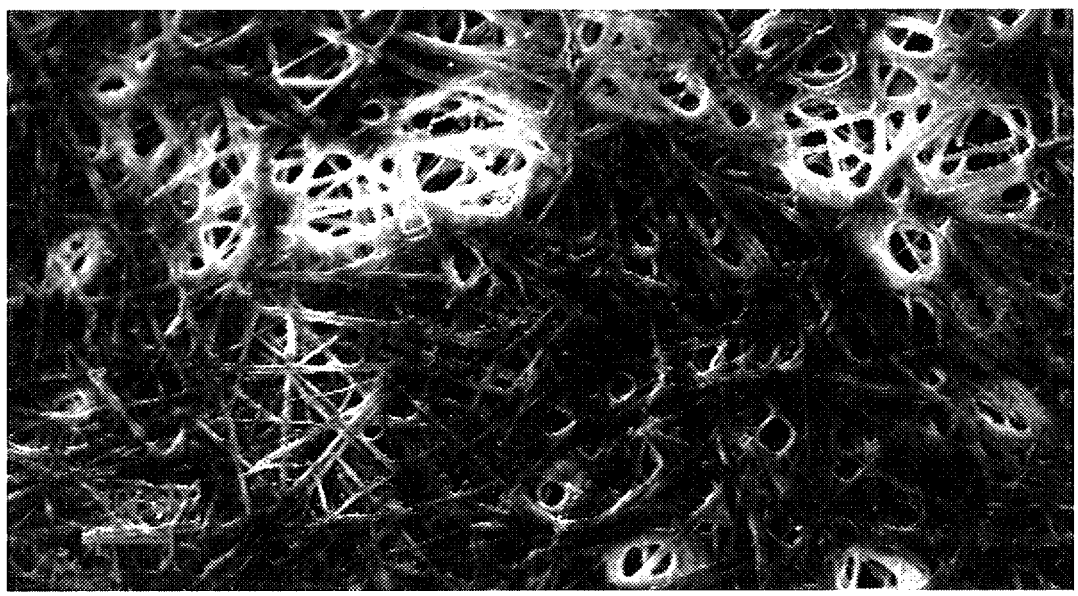

This application is a 371 of International Application PCT/IB2011/000506 filed 10 Mar. 2011 entitled "A Process For The Preparation Of Inorganic Hydrogels With Alkali Halides", which was published on 15 Sep. 2011, with International Publication Number WO 2011/110931 A1, and which claims priority from Indian Patent Application No. 579/DEL/2010 filed on 12 Mar. 2010, the content of which is incorporated herein by reference.

FIELD OF THE INVENTION

The present invention relates to a process for the preparation of inorganic hydrogels. More particularly, the present invention relates to a process for the preparation of inorganic hydrogels with alkali halides. Further, the said process relates to the preparation of inorganic hydrogels using common salt, sodium phosphate monobasic, sodium phosphate dibasic under mild reaction conditions and with the precise control of pH. The present invention also relates to the preparation of inorganic hydrogels having properties similar to natural tissue, and therefore hydrogels are extremely biocompatible and are particularly useful in biomedical and pharmaceutical applications.

BACKGROUND OF THE INVENTION

It is known that hydrogels have shown promise in many applications, mainly due to their high water content and rubbery or pliable nature, which can mimic natural tissue and can facilitate the release of bioactive substances at a desired physiological site. While the hydrogels generally have the above mentioned beneficial properties, the gel tends to shrink with time at it release the entrapped water. Therefore, the hydrogel has not only poor formulation stability but, when such a hydrogel preparation is applied to the skin, it's elicits irritable response owing to vaporization of entrapped water. Inorganic gels are well known and have long been used for various purposes, for example, for the adsorption of condensable vapors from gaseous carriers and for catalytic purposes either as a catalyst itself or as a component there of or as a carrier.

U.S. Pat. No. 5,069,816, entitled "Zirconium Silica Hydrogel Composition and Method of Preparation" wherein the methods for producing zirconium hydrophilic and hydrophobic silica hydrogel is reported. The preparations of these silica hydrogels require elevated temperature of about 800 to 1200° C. and also require elevated pressure from 100 to 500 psi. The main drawback of the given reference is towards the formation of hydrophilic and hydrophobic silica gel in the drastic conditions such as higher temperature and higher pressure applied.

U.S. Pat. No. 6,239,243 entitled "Method for Preparing Hydrophilic Silica Gels with High Pore Volume" wherein it has been reported for the preparation of hydrophilic silica hydrosol ($SiO_2$). The overall process requires elevated temperature from 90° C. to 800° C. to make the hydrophilic silica gels. The drawback of the given reference is the use of elevated temperature that should be attained under oxidizing atmosphere.

U.S. Pat. No. 4,169,926 entitled "Inorganic Hydrogels and Uses Thereof" wherein it has been reported for the preparation of silica-containing hydrogel with contacting agents comprising oxygen-containing organic compounds for catalytic purposes employing well known prior art, e.g., such as that disclosed in U.S. Pat. No. 3,887,494. In this invention titanium tetrachloride was incorporated for the preparation of inorganic hydrogels. The major drawback of this invention is the use of titanium tetrachloride which is a highly toxic and corrosive substance. On accidental release, it creates liquid pools that can either boil or evaporate.

Reference may be made to the Journal "Needle-Shape Crystal of Sodium Chloride Obtained by percrystallization" (Journal of American Chemical Society 54, 1932, p 2392), wherein it is reported that the needle like sodium chloride crystal appear in collodion bag. Further author was speculated by this method would afford a practical way of getting rid of the inorganic diffusible salts and at the same time concentrating the enzyme. Disadvantage: The involvement of sodium chloride forced for percrystallization is devoid of any other phenomena and not enough for any successful application of this process.

Reference may be made to patents U.S. Pat. No. 18,160A1 and U.S. Pat. No. 7,347,988, wherein hydrogel with ordered crystalline structure is created. This invention particularly relate to the production of crystalline hydrogel by using a major monomer is N-isopropylacrylamide and co-monomers are hydroxylethyl acrylate, allylamine, acrylic acid and other related analog and solvent is water. Disadvantage: The bottleneck in this procedure is the use of crosslinking agent for the formation of crystalline hydrogel. The pharmaceutical applications relate to the controlled delivery of active compounds for the treatment of a variety of disease requires physiological conditions for biodegradation of such crosslinking agents and to achieve the release of active entrapped compounds.

It is evident from the prior art that there are some limitations with the reported inorganic hydrogels. The preparations of such inorganic hydrogels require drastic conditions to form gels. One such condition is the temperature factor, which is very high in the prior art. Further, it is evident from the prior art that these inorganic hydrogels are not crystalline in nature and the reported crystalline hydrogels are based on organic constituents. In the present invention, we report the formation of inorganic hydrogels under ambient conditions, which can be prepared with great ease without any drastic temperature or pressure. These inorganic hydrogels also have a very special feature of crystalline in nature. The present invention for the formation of inorganic hydrogel is not only limited with sodium chloride, however, it involves other alkali halides from sodium to cesium ions. Several advantages of this invention will be apparent to those skilled in the art upon a study of this disclosure and the appended claims.

OBJECTIVES OF THE INVENTION

The primary objective of the present invention is to provide a process for the preparation of inorganic hydrogels.

Yet another objective of the present invention is to provide a process for the preparation of inorganic hydrogels with alkali halides.

Yet another objective of the present invention is to provide a simple and efficient method for preparing inorganic hydrogels by using all inorganic components under mild conditions.

Yet another objective of the present invention is to prepare inorganic hydrogels using inorganic phosphates.

Yet another objective of the present invention is the preparation of inorganic hydrogel, which are crystalline in nature.

SUMMARY OF THE INVENTION

Accordingly, the present invention relates to a process for the preparation of inorganic hydrogels of formula $M_3(H_2O)_4(PO_4)$ wherein M is selected from alkali metals for the corresponding alkali halides under mild conditions and the process comprising the steps of: (i) adding alkali halide in water and stirring for 1 to 2 minutes at temperature in the range of 30 to 35° C.; (ii) adding solution of sodium phosphate in the solution of step (i); (iii) simultaneously adding solution of alkali hydroxide in the solution of step (i); (iv) stirring the reaction mixture as obtained in step (iii) at a speed in the range of 400 to 1000 rpm for 15 to 20 minutes and maintaining the temperature in the range of 40 to 80° C.; (v) cooling the solution as obtained in step (iv) under ambient conditions for a period of 4 to 6 hours to obtain inorganic hydrogel; (vi) storing the inorganic hydrogel as obtained in step (v) for 15 to 20 hours to transform inorganic gel into crystalline form.

BRIEF DISCRIPTION OF THE DRAWINGS

FIG. 1 Scanning Electron Microscope (SEM) image for inorganic hydrogel, showing the network of hydrogel.

Figure 2:
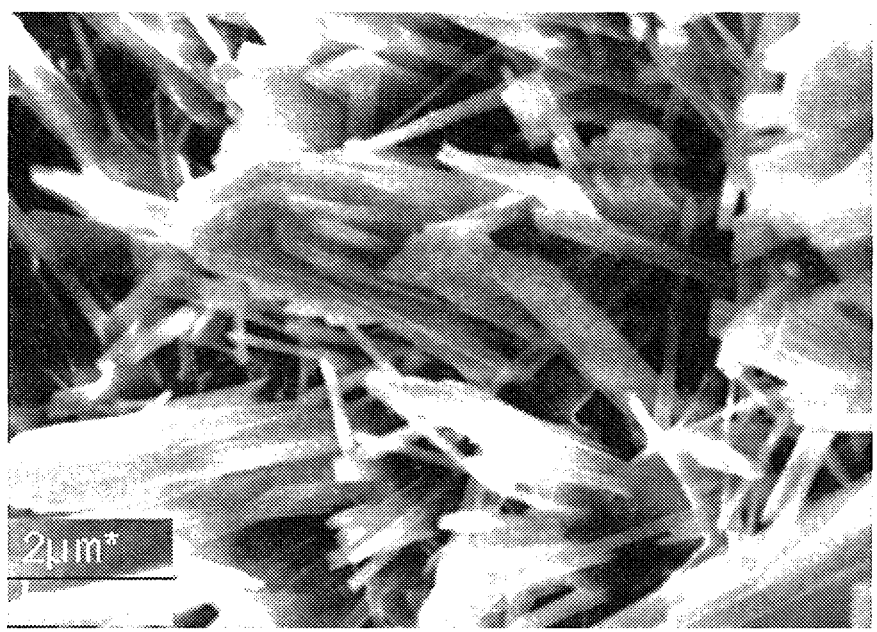

FIG. 2 Scanning Electron Microscope (SEM) image of crystalline hydrogel.

Figure 3:
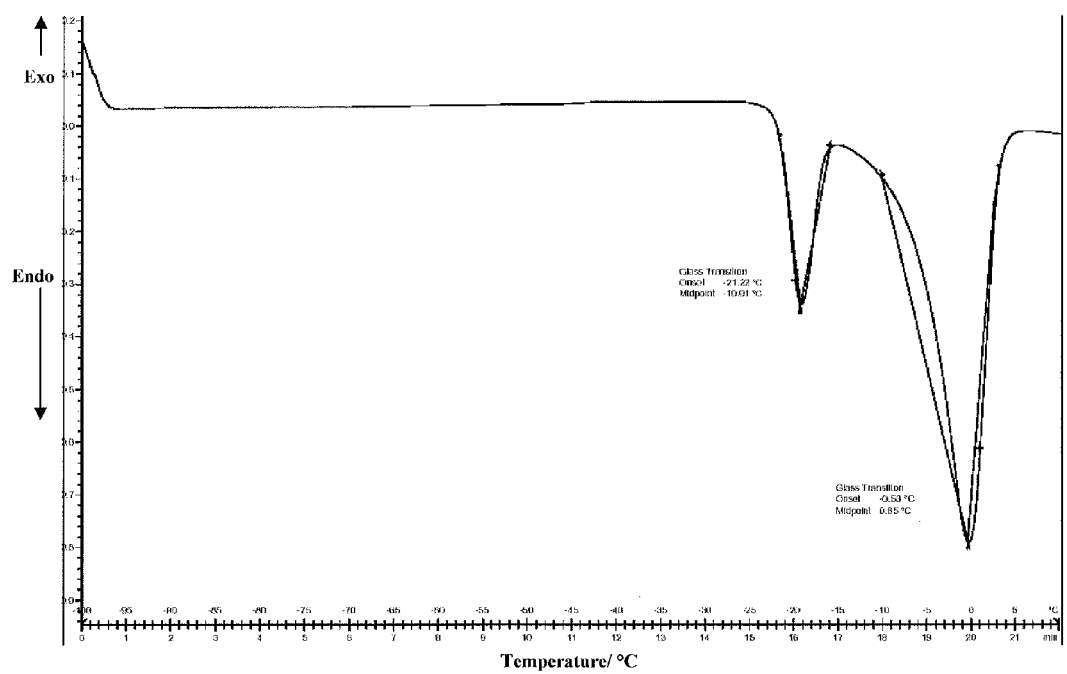

FIG. 3 Differential Scanning Calorimetry (DSC) curve for inorganic hydrogel. In the figure, two peaks can be observed: one sharp peak (peak 1) at about 0° C. and another broad peak (peak 2) at about −20° C., respectively peak 1 corresponds to the free water in hydrogel peak 2 corresponds to the bound water.

Figure 4:
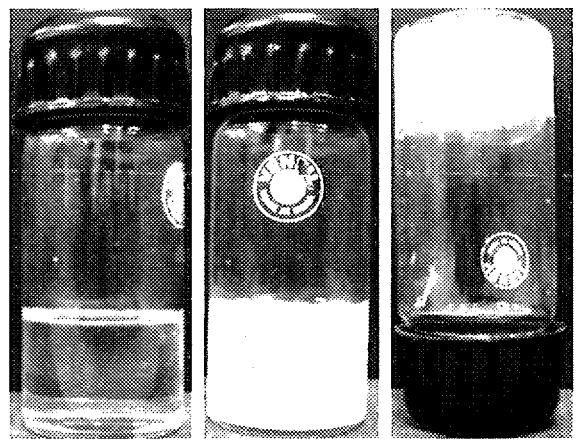

FIG. 4 showing the water absorption capacity of inorganic hydrogel in a vial/container.

DETAILED DESCRIPTION OF THE INVENTION

While the invention is susceptible to various modifications and alternative forms, specific aspect thereof has been shown by way of example and graphs and will be described in detail below. It should be understood, however that it is not intended to limit the invention to the particular forms disclosed, but on the contrary, the invention is to cover all modifications, equivalents, and alternative falling within the spirit and the scope of the invention as defined by the appended claims.

The Applicants would like to mention that the examples are mentioned to show only those specific details that are pertinent to understanding the aspects of the present invention so as not to obscure the disclosure with details that will be readily apparent to those of ordinary skill in the art having benefit of the description herein.

The terms "comprises", "comprising", or any other variations thereof, are intended to cover a non-exclusive inclusion, such that a process, catalyst composition that comprises a list of components does not include only those components but may include other components not expressly listed or inherent to such process. In other words, one or more elements in a system or process proceeded by "comprises . . . a" does not, without more constraints, preclude the existence of other elements or additional elements in the system or process.

In the following detailed description of the aspects of the invention, reference is made to the accompanying drawings and graphs that form part hereof and in which are shown by way of illustration specific aspects in which the invention may be practiced. The aspects are described in sufficient details to enable those skilled in the art to practice the invention, and it is to be understood that other aspects may be utilized and that charges may be made without departing from the scope of the present invention. The following description is, therefore, not to be taken in a limiting sense, and the scope of the present invention is defined only by the appended claims.

Accordingly, the present invention relates to a process for the preparation of inorganic hydrogels of formula $M_3(H_2O)_4(PO_4)$ wherein M is selected from alkali metals for the corresponding alkali halides under mild conditions and the said process comprising the steps of: (i) adding alkali halide in water and stirring for 1 to 2 minutes at temperature in the range of 30 to 35° C.; (ii) adding solution of sodium phosphate in the solution of step (i); (iii) simultaneously adding solution of alkali hydroxide in the solution of step (i); (iv) stirring the reaction mixture as obtained in step (iii) at a speed in the range of 400 to 1000 rpm for 15 to 20 minutes and maintaining the temperature in the range of 40 to 80° C.; (v) cooling the solution as obtained in step (iv) under ambient conditions for a period of 4 to 6 hours to obtain inorganic hydrogel; (vi) storing the inorganic hydrogel as obtained in step (v) for 15 to 20 hours to transform inorganic gel into crystalline form. In one aspect of the present invention wherein alkali metal of alkali halide is selected from the group consisting of sodium, potassium, rubidium or cesium or combination thereof. In another aspect of the present invention wherein halide is selected from the group consisting of fluoride, chloride, bromide or iodide or combination thereof In yet another aspect of the present invention wherein water used is selected from distilled water or milli -Q-water.

In yet another aspect of the present invention wherein alkali hydroxide is selected from sodium hydroxide or potassium hydroxide or combination thereof.

In yet another aspect of the present invention wherein sodium phosphate used is selected from sodium phosphate dibasic ($Na_2HPO_4 \cdot nH_2O$) or sodium phosphate monobasic ($NaH_2PO_4 \cdot nH_2O$) or combination thereof, wherein n varies in the range of 0 to 7.

In yet another aspect of the present invention wherein pH of the solution is maintained preferably in the range of 9 to 12.

In yet another aspect of the present invention, inorganic hydrogels have 100% water holding capacity.

In still another aspect of the present invention, inorganic hydrogel and its crystalline form were examined by Scanning Electron Microscopy (SEM) to show network of fiber.

In yet another aspect of the present invention, inorganic hydrogel and its crystalline form were examined by Differential Scanning Calorimeter (DSC) to show that the hydrogel to be essentially comprises freezable bound water.

Yet another aspect of the present invention wherein thus produced crystalline inorganic hydrogel is devoid of any organic entity.

In yet another aspect of the present invention wherein the preparation of inorganic hydrogel is carried out in the absence of any organic entity.

In another aspect of the present invention, the alkali halide may be in the concentration range of 0.42 to 5.1 mol/lit.

In another aspect of the present invention, sodium phosphate dibasic ($Na_2HPO_4 \cdot nH_2O$) sodium phosphate monobasic ($NaH_2PO_4 \cdot nH_2O$), where n=0-7 and the like may be selected wherein the concentration varies with n value.

In yet another aspect of the present invention, sodium phosphate dibasic ($Na_2HPO_4$) concentration is in the range of 0.70 to 1.7 mol/lit.

In yet another aspect of the present invention, sodium phosphate dibasic dihydrate ($Na_2HPO_4 \cdot 2H_2O$) concentration is in the range of 0.56 to 1.42 mol/lit.

In yet another aspect of the present invention, sodium phosphate dibasic heptahydrate ($Na_2HPO_4.7H_2O$) concentration is in the range of 0.37 to 0.93 mol/lit.

In still another aspect of the present invention, sodium phosphate monobasic ($NaH_2PO_4$) in the concentration range is 0.80 to 2.0 mol/lit.

In still another aspect of the present invention, sodium phosphate dibasic monohydrate ($NaH_2PO_4.1H_2O$) in the concentration range is 0.72 to 1.81 mol/lit.

In still another embodiment of the present invention, sodium phosphate monobasic dihydrate ($NaH_2PO_4.2H_2O$) in the concentration range is 0.64 to 1.60 mol/lit.

In still another embodiment of the present invention, alkali hydroxide such as sodium hydroxide, potassium hydroxide in the concentration range of 0.60 to 2.5 mol/lit.

Accordingly, the present invention relates to a novel, easy-to-prepare inorganic hydrogels using common salt (NaCl) and other alkali halides under very mild conditions. This process involves only inorganic constituents towards the preparation of inorganic hydrogels. The novelty of this invention relates to the crystalline nature of these inorganic hydrogels with time. This invention also relates that the role of pH is important in terms of formation and water holding capability of such inorganic hydrogels.

The present invention provides a method for the preparation of inorganic hydrogels with alkali halides which comprises of the following steps, (i) taking alkali halides in the concentration range of 0.42 to 5.1 mol/lit in milli-Q water and stirred mildly for 1 to 2 minutes at temperature in the range of 30 to 35° C. (ii) taking the solution of step (i) in reaction vessel. (iii) adding solution sodium phosphate monobasic ($NaH_2PO_4.nH_2O$) in mili-Q water in step (ii) solution, the concentration range for n=0 is 0.70 to 1.70 mol/lit in the range of 4 to 6 ml/min to step (ii), (iv) adding simultaneously the alkali hydroxide solution in step (ii) solution in the concentration range of 0.60 to 2.50 mol/lit in mili-Q water at a rate of addition in the range of 2 to 3 ml/min to step (ii), (v) stirring the reaction medium at a speed in the range of 400 to 1000 rpm, (vi) maintaining the temperature of the reaction medium in the range of 40 to 80° C. (vii) cooling the solution obtained in step vi in the temp range of 25 to 35° C. for a period of 4 to 6 h, (viii) the transformation of gel to macroscopic crystals after 15 to 20 h during storage under ambient conditions.

The inorganic hydrogels formed with alkali halides comprises the general formula $M_3(H_2O)_4(PO_4)$ where M which has an atomic number of at least 11 such as sodium, potassium, rubidium or cesium. The inorganic hydrogels of present invention can be obtained by reacting sodium phosphate monobasic ($NaH_2PO_4.nH_2O$, where n=0-7) with alkali halides, except lithium halides in presence of alkaline medium.

The amount of alkali halides to the formation of inorganic hydrogels can be in the range of 0.24 to 5.1 mol/lit, more preferably 0.85 mol/lit. However, the stability in the formation of hydrogels is highly affected by the alkalinity of the medium.

The amount of sodium phosphate monobasic ($NaH_2PO_4.nH_2O$, where n=0) to the formation of inorganic hydrogels can be in the range of 0.8 to 2.0 mol/lit preferably 1.6 mol/lit. The better stability of hydrogels occurred with higher concentration of sodium phosphate monobasic in the reaction mixture.

The inorganic hydrogels in the present invention is obtained through the addition of a clear solution of sodium phosphate monobasic ($NaH_2PO_4.nH_2O$, where n=0-7) to alkali halides, except lithium halides with a specific flow rate. Further, adding the alkali hydroxide, with a specific flow rate to the reaction mixture with a constant stirring for 15-20 minutes at around 40°-80° C. In the process, the solution pH was maintained preferably in the range of 9-12. Beyond this range of pH, there is no particular advantage and may be detrimental to the quality of gel formed. The solution is allowed for cooling at room temperature however at lower temperature will facilitate the hydrogel formation and takes less time.

In the present invention of inorganic hydrogel, sodium phosphate dibasic ($Na_2HPO_4.nH_2O$, where n=0-7) can also be used with alkali halides except lithium halides. The concentration range of sodium phosphate dibasic is 0.70 to 1.70 mol/lit preferably 1.40 mol/lit. The better stability of hydrogels occurred with higher concentration of sodium phosphate dibasic in the reaction mixture. The amount of alkali halides to the formation of inorganic hydrogels with sodium phosphate dibasic can have the range of 0.42 to 5.10 mol/lit preferably 0.85 mol/lit. However, the stability in the formation of hydrogels is highly affected by the alkalinity of the medium.

The inorganic hydrogels in the present invention is obtained through the addition of a clear solution of sodium phosphate dibasic ($Na_2HPO_4.nH_2O$, where n=0-7) to alkali halides, except lithium halides with a specific flow rate. Further, simultaneous addition of alkali metal hydroxide, with a specific flow rate to the reaction mixture under high stirring condition at 60 to 80° C. In the process, the solution pH was maintained preferably in the range of 9 to 12. Beyond this range of pH, there is no particular advantage and may be detrimental to the quality of gel formed. The solution was cooled under room temperature for the formation of gel within 3-4 h.

The alkali metal hydroxide is preferably sodium hydroxide or potassium hydroxide. However, other alkali metal of atomic number of at least 11 may be employed.

The formation of inorganic hydrogels with alkali halides and sodium phosphate dibasic/monobasic arises due to the three dimensional network, which entraps the water molecules in the void of the network through non-covalent hydrogen bonding.

The novelty of this invention lies in the preparation of inorganic hydrogels with inexpensive chemicals such as sodium chloride and sodium phosphate dibasic in a very mild condition. The prepared inorganic hydrogel leads towards crystallinity with time, which can as well be useful for many applications.

The inventive steps adopted in the present invention are (i) the present invention involves the formation of inorganic hydrogels with alkali halides under mild experimental conditions;

(ii) novel inorganic hydrogels transform to crystalline nature with time, which can be useful for many applications;

iii) this invention involved very cheap chemicals to achieve inorganic hydrogels without incorporating any transition metals;

(iv) another inventive step is the elimination of drastic temperatures and pressure in the present inorganic hydrogels;

(v) the degree of formation of inorganic hydrogels can be controlled with the concentrations of constituents involved towards the formation of such hydrogels.

EXAMPLES

The following examples are given by way of illustration and therefore should not be construed to the limit of the scope of the present invention.

Example 1

0.25 mole of sodium chloride was dissolved in 25 cc of mill-Q water and was taken in a reaction vessel. 0.16 mole of sodium phosphate monobasic ($NaH_2PO_4.nH_2O$, where n=0) was taken and dissolved in 50 cc milli-Q water. The clear solution of sodium phosphate monobasic ($NaH_2PO_4.nH_2O$, where n=0) was added in sodium chloride solution with a flow rate of 6 ml/min. Simultaneously adding the sodium hydroxide solution (0.15 mole of sodium hydroxide in 25 cc milli-Q water) with a flow rate of 3 ml/min along with a constant stirring at 700 rpm for 15 minutes at 60° C. Allowing the clear solution for cooling at 25° C. After 4 h, all the water molecules get trapped. The transition from hydrogel to gel-crystal was observed after 20 to 30 h. The gelling temperature (refers to that temperature when dramatic agglomeration or particle connection occurs) of the present hydrogel is 26° C. and melting temperature 37.5° C. Formed hydrogel were examined by Scanning Electron Microscope (SEM) (FIG. 1) and it shows that hydrogel formed a network of fibers. Further the crystalline nature (FIG. 2) of hydrogel is also observed by Scanning Electron Microscope (SEM). Differential Scanning Calorimeter shows that the hydrogel contains freezable bound water (FIG. 3).

Example 2

0.50 mole of sodium chloride was dissolved in 25 cc of mill-Q water and taken in reaction vessel. 0.16 mole of sodium phosphate monobasic ($NaH_2PO_4.nH_2O$, Where n=0) was taken and dissolved in 50 cc milli-Q water. The clear solution of sodium phosphate monobasic ($NaH_2PO_4.nH_2O$, Where n=0) was added in sodium chloride solution with flow rate 6 ml/min. Adding simultaneously the sodium hydroxide solution (0.15 mole of sodium hydroxide in 25 cc milli-Q water) with flow rate 3 ml/min. along with constant stirring at 800 rpm for 15 minutes at 60° C. Allow the clear solution for cooling at 25° C. to obtain hydrogel. Water holding capacity of the gel is 100%. After 3 h, all the water molecules get trapped. The transition from hydrogel to gel-crystal was observed after 20 to 30 h. The gelling temperature of the present hydrogel is 25° C. and melting temperature 37.5° C. Formed inorganic hydrogel were examined by Scanning Electron Microscope (SEM) and it shows that hydrogel formed a network of fibers. Differential Scanning Calorimeter shows that the hydrogel contains freezable bound water.

Example 3

0.25 mole of sodium chloride was dissolved in 25 cc of mill-Q water and taken in reaction vessel. 0.16 mole of sodium phosphate monobasic ($NaH_2PO_4.nH_2O$, Where n=0) was taken and it was dissolved in 50.0 cc milli-Q water, the clear solution of sodium phosphate monobasic ($NaH_2PO_4.nH_2O$, Where n=0) was added in sodium chloride solution with flow rate 6 ml/min. Adding simultaneously the sodium hydroxide solution (0.20 mole in 25 cc milli-Q water) with flow rate 3 ml/min. along with constant stirring at 750 rpm for 15 minutes at 60° C. Allow the clear solution for cooling at 25° C. Water holding capacity of the gel is 100%. After 3 h, all the water molecules get trapped. The transition from hydrogel to gel-crystal was observed after 20 to 30 h. The gelling temperature of the present hydrogel is 26.5° C. and melting temperature 37.5° C. Formed inorganic hydrogel were examined by Scanning Electron Microscope (SEM) and it shows that gel formed a network of fibers. Differential Scanning Calorimeter shows that the hydrogel contains freezable bound water.

Example 4

0.15 mole of cesium chloride was dissolved in 25.0 cc of mill-Q water and taken in reaction vessel. 0.16 mole of sodium phosphate monobasic ($NaH_2PO_4.nH_2O$, where n=0) was taken and it was dissolved in 50 cc milli-Q water, the clear solution of sodium phosphate monobasic ($NaH_2PO_4.nH_2O$, Where n=0) was added in cesium chloride solution with flow rate 6 ml/min. Adding simultaneously the sodium hydroxide solution (0.15 mole in 25 cc milli-Q water) with flow rate 3 ml/min. along with constant stirring at 650 rpm for 15 minutes at 60° C. Allow the clear solution for cooling at 25° C. Water holding capacity of the gel is 100%. After 5 h, all the water molecules get trapped. The transition from hydrogel to gel-crystal was observed after 20 to 30 h. The gelling temperature of the present hydrogel is 27° C. and melting temperature 37.5° C. Formed inorganic hydrogel were examined by Scanning Electron Microscope (SEM) and it shows that gel formed a network of fibers. Differential Scanning Calorimeter shows that the hydrogel contains freezable bound water.

Example 5

0.33 mole of cesium chloride was dissolved in 25 cc of mill-Q water and taken in reaction vessel. 0.16 mole of sodium phosphate monobasic ($NaH_2PO_4.nH_2O$, where n=0) was taken and it was dissolved in 50 cc milli-Q water, the clear solution was added in cesium chloride solution with flow rate 6 ml/min. Adding simultaneously the sodium hydroxide solution (0.15 mole in 25 cc milli-Q water) with flow rate 3 ml/min. along with constant stirring for 15 minutes at 60° C. Allow the clear solution for cooling at 25° C. Water holding capacity of the gel is 100%. After 4 h, all the water molecules get trapped. The transition from hydrogel to gel-crystal was observed after 20 to 30 h. All water molecules get trapped. The gelling temperature of the present hydrogel is 27.5° C. and melting temperature 37.5° C. Formed inorganic hydrogel were examined by Scanning Electron Microscope (SEM) and it shows that gel formed a network of fibers. Differential Scanning Calorimeter shows that the hydrogel contains freezable bound water.

Example 6

0.15 mole of cesium chloride was dissolved in 25 cc of mill-Q water and taken in reaction vessel. 0.16 mole of sodium phosphate monobasic ($NaH_2PO_4.nH_2O$, where n=0) was taken and it was dissolved in 50 cc milli-Q water, the clear solution was added in cesium chloride solution with flow rate 6 ml/min. Adding simultaneously the sodium hydroxide solution (0.20 mole in 25 cc milli-Q water) with flow rate 3 ml/min along with constant stirring for 15 minutes at 60° C. Allow the clear solution for cooling at 25° C. Water holding capacity of the gel is 100%. After 5 h, all the water molecules get trapped. The transition from hydrogel to gel-crystal was observed after 20 to 30 h. The gelling temperature of the present hydrogel is 28° C. and melting temperature 37.5° C. Formed inorganic hydrogel were examined by Scanning Electron Microscope (SEM) and it shows that gel formed a network of fibers. Differential Scanning Calorimeter shows that the hydrogel contains freezable bound water.

Example 7

0.85 mole of sodium chloride was dissolved in 25 cc of mill-Q water and taken in a reaction vessel. 0.13 mole of sodium phosphate monobasic ($NaH_2PO_4.2H_2O$, where n=2), was taken and dissolved in 50 cc milli-Q water. The clear solution of sodium phosphate monobasic was added in sodium chloride solution with a flow rate of 5 ml/min. Simultaneously, sodium hydroxide solution (0.12 mole in 25 cc milli-Q water) with a flow rate of 3 ml/min was added with a constant stirring for 20 minutes at 70° C. Allowed the clear solution for cooling at 25° C. After 10 h, water molecules get trapped. The transition from hydrogel to gel-crystal was observed after 20 to 30 h. The gelling temperature of the present hydrogel is 28° C. and the melting temperature is 37° C.

Example 8

0.14 mole of sodium chloride was taken and it was dissolved in 25 cc of mill-Q water in a reaction vessel. 0.12 mole of sodium phosphate monobasic ($NaH_2PO_4.2H_2O$, where n=2) was taken and dissolved in 50 cc milli-Q water. The clear solution of sodium phosphate monobasic was added in sodium chloride solution with a flow rate of 5 ml/min. simultaneously; sodium hydroxide solution (0.20 mole in 25 cc milli-Q water) with a flow rate of 3 ml/min. at a constant stirring for 20 minutes at 65° C. was added. Allowing the clear solution for cooling at 25° C. After 18 h, all the water molecules get trapped. The transition from hydrogel to gel-crystal was observed after 20 to 30 h. The gelling temperature of the present hydrogel is 27° C. and the melting temperature is 36° C.

Example 9

0.12 mole of sodium chloride was dissolved in 25 cc of mill-Q water and taken in a reaction vessel. 0.16 mole of sodium phosphate dibasic ($Na_2HPO_4$) was taken and dissolved in 50 cc milli-Q water. The clear solution of sodium phosphate dibasic was added in sodium chloride solution with a flow rate of 5 ml/min. Simultaneously sodium hydroxide solution (0.17 mole in 25 cc milli-Q water) was added with a flow rate of 3 ml/min. at a constant stirring for 20 minutes at 65° C. Allowing the clear solution for cooling at 25° C. After 18 h, all the water molecules get trapped. The transition from hydrogel to gel-crystal was observed after 20 to 30 h. The gelling temperature of the present hydrogel is 27° C. and the melting temperature is 36° C. Differential Scanning Calorimeter shows that the hydrogel contains freezable bound water.

Example 10

0.14 mole of sodium chloride was dissolved in 25 cc of mill-Q water and taken in a reaction vessel. 0.12 mole of sodium phosphate dibasic heptahydrate ($Na2HPO4.7H2O$) was taken and dissolved in 50 cc milli-Q water. The clear solution of sodium phosphate dibasic heptahydrate was added in sodium chloride solution with a flow rate of 3 ml/min. Simultaneously sodium hydroxide solution (0.20 mole in 25 cc milli-Q water) was added with a flow rate of 3 ml/min. at a constant stirring at 900 rpm for 20 minutes at 60° C. Allowing the clear solution for cooling at 25° C. After 20 h, water molecules get trapped. The transition from hydrogel to gel-crystal was observed after 30 to 35 h. The gelling temperature of the present hydrogel is 27° C. and the melting temperature is 36° C.

In order to determine the water holding capacity of the hydrogel the inventors have done trials, wherein thus prepared inorganic hydrogel is allowed to expose with different proportion in the range of 1:10 to 1:90 of water, and, it has been observed that in all the experiments, thus produced inorganic hydrogel is capable of absorbing 100% water.

ADVANTAGES OF THE INVENTION

The main advantages of the present invention are
i) Novel inorganic hydrogels are achievable with inexpensive reagents under very mild conditions and in the absence of any organic entity.
ii) The present invention resulted in inorganic hydrogels having application as a natural tissue, and is extremely biocompatible and is particularly useful in biomedical and pharmaceutical applications.
iii) These inorganic hydrogels can be useful during the purification process of salt rich enzymes or proteins. Marine bacteria grown in salt rich medium, during the enzyme production alkali halide salts are present in the enzymes or proteins.

The advantages of the disclosed invention are thus attained in an economical, practical, and facile manner. While preferred aspects and example configurations have been shown and described, it is to be understood that various further modifications and additional configurations will be apparent to those skilled in the art. It is intended that the specific embodiments and configurations herein disclosed are illustrative of the preferred nature and best mode of practicing the invention, and should not be interpreted as limitations on the scope of the invention.

We claim:

1. A process for the preparation of an inorganic hydrogel of formula $M_3(H_2O)_4(PO_4)$ wherein M is selected from alkali metals for the corresponding alkali halides under mild conditions and the process comprising the steps of:
   (i) adding alkali halide in water, a solution of sodium phosphate and a solution of alkali hydroxide and stirring for 1 to 2 minutes at temperature in the range of 30 to 35° C.;
   (ii) stirring the reaction mixture as obtained in step (i) at a speed in the range of 400 to 1000 rpm for 15 to 20 minutes and maintaining the temperature in the range of 40 to 80° C.;
   (iii) cooling the solution as obtained in step (ii) for a period of 4 to 6 hours to obtain inorganic hydrogel; and
   (iv) storing the inorganic hydrogel as obtained in step (iii) for 15 to 20 hours to transform the inorganic hydrogel into crystalline form.

2. The process as claimed in claim 1, wherein in step (i) alkali metal of alkali halide is selected from the group consisting of sodium, potassium, rubidium and cesium and a combination thereof.

3. The process as claimed in claim 1, wherein in step (i) the halide is selected from the group consisting of fluoride, chloride, bromide and iodide and a combination thereof.

4. The process as claimed in claim 1, wherein in step (i) sodium phosphate is monobasic ($NaH_2PO_4.nH_2O$) or dibasic ($Na_2HPO_4.nH_2O$) or a combination thereof, wherein n is in the range of 0 to 7.

5. The process as claimed in claim 1, wherein in step (i) pH of the solution is maintained in the range of 9 to 12.

6. The process as claimed in claim 1, wherein the alkali hydroxide is sodium hydroxide, potassium hydroxide or both.

7. The process as claimed in claim 1, wherein in step (iii) the inorganic hydrogel has 100% water holding capacity.

8. The process as claimed in claim 1, wherein the inorganic hydrogel of step (iii) has a network of fiber.

9. The process as claimed in claim 1, wherein the crystalline inorganic hydrogel comprises freezable bound water.

10. The process as claimed in claim 1, wherein the crystalline inorganic hydrogel is devoid of any organic entity.

11. The process as claimed in claim 1, wherein the process is carried out in the absence of any organic entity.

* * * * *